United States Patent
Heinar

(10) Patent No.: US 8,618,175 B2
(45) Date of Patent: Dec. 31, 2013

(54) ULTRASOUND MEDICAL GEL COMPOSITION ETHERIFIED HYDROXYETHYLCELLULOSE

(75) Inventor: Thomas Heinar, Toronto (CA)

(73) Assignee: Brussels Ventures Corp., Scarborough, Ontario (CA)

( * ) Notice: Subject to any disclaimer, the term of this patent is extended or adjusted under 35 U.S.C. 154(b) by 0 days.

(21) Appl. No.: 13/638,080

(22) PCT Filed: Jul. 18, 2011

(86) PCT No.: PCT/CA2011/000829
§ 371 (c)(1), (2), (4) Date: Sep. 28, 2012

(87) PCT Pub. No.: WO2012/009794
PCT Pub. Date: Jan. 26, 2012

(65) Prior Publication Data
US 2013/0116331 A1    May 9, 2013

Related U.S. Application Data

(60) Provisional application No. 61/365,444, filed on Jul. 19, 2010.

(51) Int. Cl.
*A61K 31/14*    (2006.01)

(52) U.S. Cl.
USPC ............ 514/643; 514/772; 514/781; 514/944

(58) Field of Classification Search
USPC .................................. 514/643, 772, 781, 944
See application file for complete search history.

(56) References Cited

U.S. PATENT DOCUMENTS

2002/0061864 A1    5/2002    Livingston et al.
2010/0069601 A1*   3/2010    Baumer ................... 528/322

FOREIGN PATENT DOCUMENTS

| EP | 1793860 A1 | 6/2007 |
| FR | 2770402 A1 | 5/1999 |
| WO | 2007038855 A1 | 4/2007 |

OTHER PUBLICATIONS

Harvey Fishman. Happi Magazine, Dec. 2008, p. 40.*
Durham et al. Personal Care, Sep. 2010, pp. 73-76.*
Tylose—PersonalCareApplications.
Tylose—ShinEtsu.
Zemea—TheNaturatChoice.
Abstract; A.K. Nashima et al: "Survival of *Serratia marcescens* in benzalkonium chloride and in multiple-dose medication vials: relationship to epidemic septic arthritis", J Clin Microbiol., Jun. 1987: 25(6), pp. 1019-1021.
Sing et al.: "Influence of Cellulolytic Bacterial Augmentation on Organic Carbon and Available Phosphorus in Sandy Loam Soil under Cultivation", Journal of Agricultural Science, vol. 2 .No. 3: Sep. 2010.
Abstract; Nagai et al.: "Biochemical characterization of a *Pseudomonas fluorescens* strain isolated from a benzalkonium chloride solution", Biol Pharm Bull, 1996 Jun; 19(6), pp. 873-5;.

* cited by examiner

*Primary Examiner* — Savitha Rao
*Assistant Examiner* — Angela Brown-Pettigrew
(74) *Attorney, Agent, or Firm* — Philip C. Mendes da Costa; Bereskin & Parr LLP/S.E.N.C.R.L., s.r.l.

(57) ABSTRACT

Ultrasound medical gel composition, the compositions comprising: (a) a gelling agent comprising etherified hydroxyethylcellulose; (b) an antimicrobial agent, specifically the quaternary ammonium compound benzalkonium chloride; (c) a solvent, 1,3-propanediol being preferred; and (d) water.

8 Claims, No Drawings

ULTRASOUND MEDICAL GEL COMPOSITION ETHERIFIED HYDROXYETHYLCELLULOSE

FIELD

The disclosure relates to medical gels, such as those for use in ultrasound procedures. Specifically, the disclosure relates to antimicrobial medical gels, and to methods for producing such antimicrobial medical gels.

INTRODUCTION

The following is not an admission that anything discussed below is prior art or part of the common general knowledge of persons skilled in the art.

Medical gels are commonly used for dermal ultrasound, physiotherapy, medical aesthetic procedures, and other related procedures, and are used both as a lubricant and couplant between a transducer (or probe) and the skin Typical medical gels are considered "bacteriostatic" as they contain preservatives that prevent bacterial growth during storage. However, preservatives only restrict bacteria growth, and do not reduce or kill bacteria to which the gel is exposed during a procedure. Furthermore, preservatives do not inhibit the transfer of bacteria from an infected patient to the transducer or probe during a procedure. Accordingly, medical gels can present a serious risk of infection, as a vehicle for cross-contamination. Numerous cases of nosocomial pathogens, such as bacteremia, septicaemia, *B. cepacia* complex, Methicillin-Susceptible *Staphylococcus aureus* and *Klebsiella pneumoniae* have been traced back to medical gels contaminated by infected patients (1, 2, 3). Nosocomial infections result in over 100,000 deaths per year and costs the US & Canadian healthcare systems over $30 billion per year (4, 5, 6, 7). In turn, hospitals are increasing efforts to reduce nosocomial rates in order to save lives and lower the financial burden of treating infected patients (7, 8, 9). There is also a growing concern that nosocomial infections present a growing threat of litigation for the healthcare institution (10).

To eliminate surface pathogens, some medical equipment is sterilized between patient procedures by means of autoclave (steam), gas (chemical) or ultrasonic bath. However, these methods cannot be used to disinfect transducers and probes, as the internal circuitry and materials of these devices are extremely sensitive to heat, chemicals and mechanical vibrations. As such, manufacturers are explicit in their instructions not to use such methods of sterilization, as they would damage and/or alter the performance of the equipment.

Instead, medical staff are often instructed to use mild solvents, various cleaning sprays, and wipes to disinfect transducers and probes between procedures. Such cleansing protocols do not address the risk of cross-contamination that can occur during a procedure, between the patient, medical gel, transducer and other fomites (11, 12, 13). Furthermore, they do not address what environmental investigations have revealed as a source of contamination—the medical gel. As such, transmission of pathogens from patient to patient via the medical gel can still occur.

In order to mitigate the risk of cross-contamination during ultrasound and other topical procedures, attempts have been made to produce antimicrobial medical gels which would kill the bacteria that the gel is exposed to during use. For example, International Patent Application Publication No. WO 2007/038855 (O'Reilly et al.) discloses a medical antimicrobial gel useful as a coupling media and lubricant for light-based or ultrasound cutaneous procedures, comprised of a solvent, a thickener and an antimicrobial agent and preferably a bioadhesive and humectant.

SUMMARY

The following summary is provided to introduce the reader to the more detailed discussion to follow. The summary is not intended to limit or define the claims.

According to one aspect, a medical gel comprises a) a gelling agent comprising etherified hydroxyethylcellulose; b) an antimicrobial agent; c) a solvent; and d) water.

The etherified hydroxyethylcellulose may be present in the medical gel at between 1 wt % and 4 wt %. More specifically, the etherified hydroxyethylcellulose may be present in the medical gel at between 2.2 wt % and 2.7 wt %.

At least some of the repeating units of the etherified hydroxyethylcellulose may be of the formula:

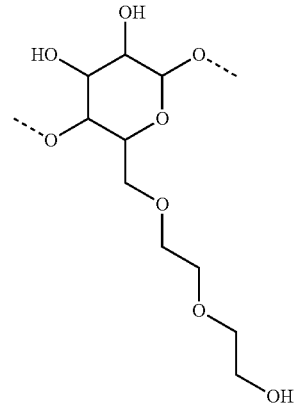

In one particular example, the etherified hydroxyethylcellulose may be of the formula:

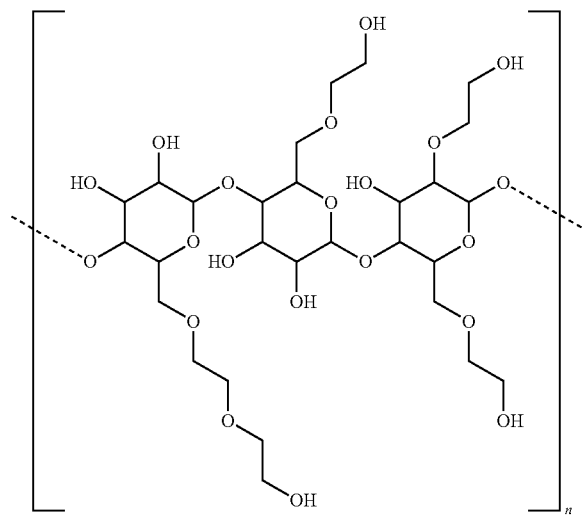

The viscosity of the etherified hydroxyethylcellulose may be about 100,000 cps when in a 2% aqueous solution.

The antimicrobial agent may be a quaternary ammonium compound. For example, the antimicrobial agent may be benzalkonium chloride. The antimicrobial agent may present in the medical gel at between 0.090 wt % and 0.110 wt %. More specifically, the antimicrobial agent may be present in the medical gel at between 0.095 wt % and 0.105

The gelling agent may be hydroxyethylcellulose, or etherified hydroxyethylcellulose. The gelling agent may be present in the medical gel at between 1 wt %.

The solvent may be a non-petroleum solvent. For example, the solvent may be propanediol. The solvent may be present in the medical gel at between 3.0 wt % and 3.5 wt %. More specifically, the solvent may be present in the medical gel at between 3.1 wt % and 3.3 wt %.

The water may be present in the medical gel at 80 wt % to 99 wt %. More specifically, the water may be present in the medical gel at 93 wt % to 96 wt %.

According to another aspect, a medical gel comprises a) a solvent comprising propanediol; b) a gelling agent; c) an antimicrobial agent; and d) water.

The propanediol may present in the medical gel at between 3.0 wt % and 3.5 wt %. More specifically, the propanediol may be present in the medical gel at between 3.1 wt % and 3.3 wt %.

The gelling agent may present in the medical gel at between 1 wt % and and 4 wt %. More specifically, the gelling agent may be present in the medical gel at between 2.2 wt % and 2.7 wt %.

At least some units of the gelling agent may be of the formula:

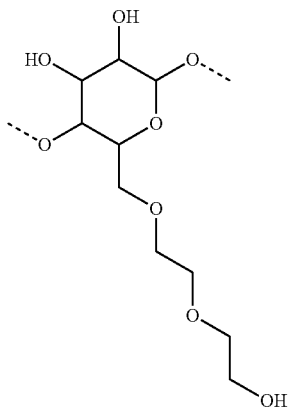

In some particular examples, the gelling agent may be of the formula:

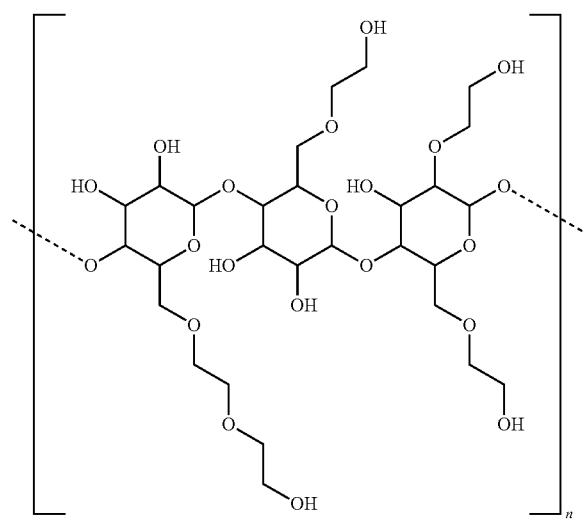

The viscosity of the gelling agent may be about 100,000 cps when in a 2% aqueous solution.

The antimicrobial agent may be a quaternary ammonium compound. For example, the antimicrobial agent may be benzalkonium chloride. The antimicrobial agent may be present in the medical gel at between 0.090 wt % and 0.110 wt %. More specifically, the antimicrobial agent may be present in the medical gel at between 0.095 wt % and 0.105 wt %.

The water may be present in the medical gel at 80 wt % to 99 wt %. More specifically, the water may be present in the medical gel at 93 wt % to 96 wt %.

According to another aspect, a medical gel comprises a) etherified hydroxyethylcellulose present in the medical gel at 1 wt % to 4 wt %; b) benzalkonium chloride present in the medical gel at 0.090 wt % to 0.110 wt %; c) propanediol present in the medical gel at 3.0 wt % to 3.5 wt %; and d) water present in the medical gel at 80 wt % to 99 wt %.

DETAILED DESCRIPTION

Various apparatuses or processes will be described below to provide an example of an embodiment of each claimed invention. No embodiment described below limits any claimed invention and any claimed invention may cover processes or apparatuses that are not described below. The claimed inventions are not limited to apparatuses or processes having all of the features of any one apparatus or process described below or to features common to multiple or all of the apparatuses described below. It is possible that an apparatus or process described below is not an embodiment of any exclusive right granted by issuance of this patent application. Any invention disclosed in an apparatus or process described below and for which an exclusive right is not granted by issuance of this patent application may be the subject matter of another protective instrument, for example a continuing patent application, and the applicants, inventors or owners do not intend to abandon, disclaim or dedicate to the public any such invention by its disclosure in this document.

A medical gel suitable for use in dermal ultrasound, physiotherapy, medical aesthetic procedures, and other related procedures preferably meets several criteria. Particularly, the medical gel is preferably (1) clear, so that the skin can be viewed through the gel; (2) resistant to drying, so that the gel does not dry out; and (3) of sufficient spreading ability, so that it may be spread across the skin. Additional preferable properties include (1) lubricity, so that the gel may lubricate the skin; (2) viscosity and adherence, so that the gel does not flow off of the skin; (3) tolerable acidity, so that the medical gel does not irritate the skin (4) pseudoplasticity, so that the medical gel may be dispensed (5) and (5) minimal aeration so that any excessive air entrainment as tiny bubbles would not potentially interfere with instrument transmissions through the gel. Furthermore, a medical gel that is used in ultrasound is preferably non-reflective and non-refractive to ultrasound waves, so that it does not cause image distortion during ultrasound procedures.

Medical gels currently in use generally meet the above criteria. However, this is not the case for antimicrobial medical gels. Specifically, although attempts have been made to produce medical gels that are antimicrobial, Applicant is not aware of any that have been able to meet the criteria outlined above. For example, as set out in the Examples section below, Applicant has conducted numerous tests on the various components of the antimicrobial gel disclosed by O'Reilly et al. (mentioned above). Based on these tests, it is believed that the antimicrobial gel described by O'Reilly et al. is relatively turbid, and would not be sufficiently clear for use as a medical gel. Furthermore, it is believed that the antimicrobial gel described by O'Reilly et al. is not sufficiently resistant to drying for use as a medical gel. Finally, it is believed that the antimicrobial gel described b O'Reilly et al. is not sufficiently spreadable for use as a medical gel. Accordingly, it is believed that the antimicrobial gel disclosed by O'Reilly et al. would not be ideal or preferable for use in dermal ultrasound, physiotherapy, medical aesthetic procedures, and other related procedures.

The present disclosure provides an antimicrobial medical gel that is believed to meet the above criteria (as set out in the Examples section below), and is therefore believed to be suitable for use in dermal ultrasound, physiotherapy, medical aesthetic procedures, and other related procedures.

An antimicrobial medical gel of the present disclosure generally includes (a) a gelling agent; (b) an antimicrobial agent; (c) a solvent; and (d) water.

In some examples, the gelling agent is present in the medical gel at between 1 wt % and 4 wt %, and more particularly at between 2.20 wt % and 2.70 wt %. The antimicrobial agent may be present in the medical gel at between 0.090 wt % and 0.110 wt %, and more particularly at between 0.095 wt % and 0.105 wt %. The solvent may be present in the medical gel at between 3.0 wt % and 3.5 wt %, and more particularly at between 3.1 wt % and 3.3 wt %. The water may be present at between about 80 wt % and 99 wt %, and more particularly at between 93 wt % and 99 wt %.

In some examples, the gelling agent may be hydroxyethylcellulose. In some particular examples, the gelling agent may be an etherified hydroxyethylcellulose. As used herein, the term "etherified hydroxyethylcellulose" refers to a hydroxyethylcellulose in which at least one of the substituents of at least some of the repeating units includes more than one ether group. For example, hydroxyethylcellulose may generally be represented by the following formula (although other formulas are possible):

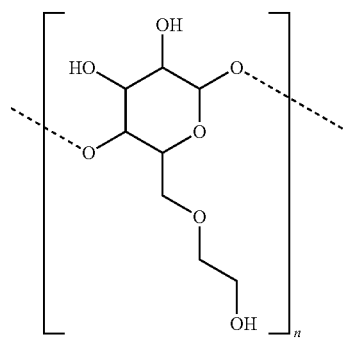
(1)

In an exemplary etherified hydroxyethylcellulose, at least some of the repeating units of the molecule shown in formula (1) are replaced with the following:

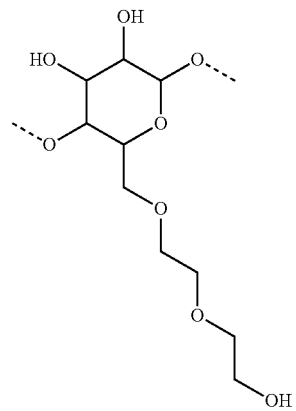
(2)

As can be seen above, in formula (2), the substituent includes a second ether group, as compared to formula (1).

In one particular example, the etherified hydroxyethylcellulose may be of the following formula:

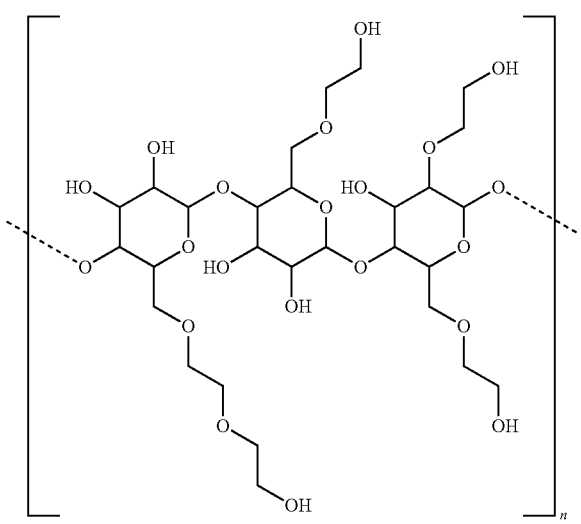
(3)

One suitable etherified hydroxyethylcellulose in accordance with formula (3) is sold by ShinEtsu Chemical Co. Ltd. (Tokyo, Japan) under the name Tylose® HS 100000 YP2. This particular etherified hydroxyethylcellulose has a viscosity of about 100,000 cps when in a 2% aqueous solution, and has a particle size of less than 180 microns.

As outlined in the Examples section below, the use of an etherified hydroxyethylcellulose is believed to yield product that is suitable for use as an antimicrobial medical gel.

Specifically, the use of an etherified hydroxyethylcellulose is believed to yield an antimicrobial medical gel that is of sufficient clarity, as compared to other antimicrobial medical gels.

In alternate examples, an alternate suitable gelling agent may be used.

In some examples, the antimicrobial agent of the antimicrobial medical gel may be a quaternary ammonium compound, such as benzalkonium chloride. One suitable benzalkonium chloride is sold by Stepan Company (Northfield, Ill.) under the brand name Stepanquat® 50 NF. Alternatively, the antimicrobial agent may be another quaternary ammonium compound, such as Chlorhexidine or Cetylpyridinium Chloride.

In further alternate examples, the antimicrobial agent may be Chlorobutanol, Chloroxylinol, Triclosan, or Cetrimide (Alkylmethyl ammonium Bromide).

In some examples, the solvent of the antimicrobial medical gel is a non-petroleum solvent (i.e. not propylene glycol or butylene glycol). For example, the solvent may be propanediol. One suitable propanediol is sold by Dupont under the brand name Zemea™. As outlined in the examples section hereinbelow, the use of propanediol as a solvent is believed to yield product that is suitable for use as an antimicrobial medical gel. Specifically, the use of propanediol as a solvent is believed to yield an antimicrobial medical gel that is clearer, more resistant to drying, and has better spreading properties than other antimicrobial medical gels.

Alternate suitable non-petroleum solvents include water soluble dispersants, surfactants such as polysorbates, polyethylene glycols, or diglycerol.

In alternate examples, the solvent may be a petroleum solvent.

The antimicrobial medical gel of the present disclosure may optionally include various additional optional components, such as anaesthetics, odor masking agents, bioadhesives, or moisturizers.

In order to prepare an antimicrobial medical gel, the gelling agent may be dispersed in the water, with agitation and heat. For example, the gelling agent and the water may be mixed for approximately 10 to 20 minutes. In alternate examples, the time required for mixing may be less than 10 minutes, or greater than 20 minutes, depending on the batch size. While mixing, the mixture may be heated to between approximately 65 and 75 degrees Celsius, and more specifically, approximately 70 degrees Celsius. The mixture may then be cooled to below approximately 50 degrees Celsius.

In alternate examples, after dispersing the gelling agent in the water, the resulting mixture may alternately or additionally be treated with an alkali, and then acidified.

The solvent may be mixed with the antimicrobial agent until the antimicrobial agent is dissolved. The solution may then be added to the mixture of the water and the gelling agent, and the resultant combination may be mixed until it is generally uniform and a viscous mass is achieved. The mixing may optionally be carried out slowly to avoid incorporation of air.

EXAMPLES

Example 1

An antimicrobial medical gel was prepared as set out above, with the following composition:
Gelling agent: 2.6 wt % etherified hydroxyethylcellulose (ShinEtsu Tylose® HS 100000 YP2);
Antimicrobial agent: 0.2 wt % benzalkonium chloride (Stepanquat® 50 NF);
Solvent: 3.2 wt % propanediol (Dupont Zemea™); and
Water: 94 wt %.

The antimicrobial medical gel was tested for antimicrobial effectiveness (USP 51) as a Category 1 product by GAP EnviroMicrobial services (London, Ontario, Canada). This test requires no increase (i.e. not more than 0.5 log 10 units higher) at 28 days in yeasts and moulds from the initial calculated count; and not less than 3.0 log reduction at 28 days in bacteria from the calculated count. The test indicated that the antimicrobial medical gel meets the requirements for antimicrobial effectiveness as required by USP 51.

Example 2

The turbidity of various aqueous solutions of different gelling agents was measured. Tests were carried out both with and without 0.1 wt % benzalkonium chloride in the solution. A control sample of Aquasonic Clear Ultrasound gel was used as a control. Turbidity was measured using the Hack Model 2100 Laboratory Turbidimeter. The results are shown below in table 1.

TABLE 1

Turbidity for various gelling agents

| Test No. | Gelling Agent Type | Wt % in Solution | Benzalkonium Chloride wt % | Turbidity (NTU) |
|---|---|---|---|---|
| 1 | Control - Aquasonic Clear Ultrasound Gel | | | 51.4 |
| 2 | Cellosize ™ PCG10 Hydroxyethylcellulose | 0.26 | 0 | 532 |
| 3 | Natrosol ® 250 HHR Hydroxyethylcellulose | 0.26 | 0 | 10.8 |
| 4 | Natrosol ® 250 HHR Hydroxyethylcellulose | 1.0 | 0.1 | 192 |
| 5 | ShinEtsu Tylose ® HS 100000YP2 HEC | 0.26 | 0 | 7.39 |
| 6 | ShinEtsu Tylose ® HS 100000YP2 HEC | 1.0 | 0.1 | 14.7 |

As mentioned hereinabove, ShinEtsu Tylose® HS 100000YP2 HEC is an etherified hydroxyethylcellulose corresponding to formula (3) above. Natrosol 250 HHR hydroxyethylcellulose is not an etherified hydroxyethylcellulose.

Surprisingly, the results shown in table 1 indicate that aqueous solutions prepared with etherified hydroxyethylcellulose, and particularly with etherified hydroxyethylcellulose according to formula (3) above, are less turbid (i.e. more clear) than solutions prepared with other types of hydroxyethylcellulose. Based on the results in table 1, it is believed that antimicrobial medical gels prepared with etherified hydroxyethylcellulose, and particularly with etherified hydroxyethylcellulose according to formula (3) above, will exhibit less turbidity (i.e. more clarity) than other antimicrobial medical gels.

Example 3

The turbidity of various gels having various solvents was measured. All gels were prepared as described hereinabove. All gels were made with ShinEtsu Tylose® HS 100000YP2 HEC etherified hydroxyethylcellulose as a gelling agent. All gels were made with benzalkonium chloride as an antimicrobial agent. Turbidity was measured using the Hack Model 2100 Laboratory Turbidimeter. The results are shown below in table 2.

TABLE 2

Turbidity for various solvents

| Test No. | Solvent Type | Wt % | Gelling Agent wt % | Anti- microbial Agent wt % | Water wt % | Turbidity (NTU) |
|---|---|---|---|---|---|---|
| 1 | — | 0 | 2.6 | 0.1 | to 100 | 154 |
| 2 | Propanediol (Zemea ™) | 3.2 | 2.6 | 0.1 | to 100 | 77.3 |
| 3 | Propylene Glycol | 3.2 | 2.6 | 0.1 | to 100 | 92.7 |
| 4 | Glycerin 99% | 3.2 | 2.6 | 0.1 | to 100 | 252 |

Surprisingly, the results shown in table 2 indicate that antimicrobial medical gels prepared with propanediol are less turbid (i.e. more clear) than antimicrobial medical gels prepared with other solvents, including petroleum solvents.

Example 4

The drying resistance of various gels having various solvents was measured. All gels were prepared as described hereinabove. All gels were made with ShinEtsu Tylose® HS 100000YP2 HEC etherified hydroxyethylcellulose as a gelling agent. All gels were made with benzalkonium chloride as an antimicrobial agent. Drying resistance was measured by weighing a known amount of the sample onto a glass slide, and placing the weighed slide into an incubator oven set at 38 degrees Celsius. The slide was removed and weighed at two hour intervals. The results are shown below in table 3.

TABLE 3

Drying Resistance for various solvents

| Test No. | Solvent Type | Wt % | Gelling Agent wt % | Antimicrobial Agent wt % | Water wt % | Weight (g) After Set Period of Time 0(h) | 2(h) | 4(h) | 6(h) | % Decrease in Weight after 6 h |
|---|---|---|---|---|---|---|---|---|---|---|
| 1 | — | 0 | 2.6 | 0.1 | to 100 | 4.88 | 4.49 | 4.19 | 418 | 14.3 |
| 2 | Propanediol (Zemea ™) | 3.2 | 2.6 | 0.1 | to 100 | 4.67 | 4.26 | 4.12 | 4.11 | 12.0 |
| 3 | Propylene Glycol | 3.2 | 2.6 | 0.1 | to 100 | 5.14 | 4.66 | 4.41 | 4.33 | 15.8 |
| 4 | Glycerin 99% | 3.2 | 2.6 | 0.1 | to 100 | 5.36 | 4.71 | 4.38 | 4.19 | 21.8 |

Surprisingly, the results shown in table 3 indicate that antimicrobial medical gels prepared with propanediol exhibit better drying resistance than antimicrobial medical gels prepared with other solvents, including non-petroleum solvents.

Example 5

The spreading ability of various solvents was measured. Solvents including an antimicrobial agent, as well as solvents without an antimicrobial agent, were tested. Benzalkonium chloride was used as an antimicrobial agent. Spreading ability was measured by dropping one drop of liquid onto Standard No. 1 filter paper, and measuring the diameter of each drop at various time periods. The results are shown below in table 3, and reflect the average results obtained after 3 trials for each sample.

In practicality, the period of optimum physical performance required of the medical gel would be of a duration of considerably less than that observed for the spreading ability test. However, the results demonstrate the balance between solvent density, humectancy, and spreadability. Glycerin, since it is significantly more dense than the other solvents, exhibited a very small initial droplet diameter. It is believed that the relative percentage change in size of the glycerin droplets was created due to the great humectant ability of glycerin. Rapid humectancy however does not aid in short term lubricity, and may result with undue tackiness of the gel, as well as longer term drying of surrounding substrates.

Example 6

Three samples of antimicrobial medical gel were prepared as set out above, with the following composition:

Gelling agent: 2.6 wt % etherified hydroxyethylcellulose (ShinEtsu Tylose® HS 100000 YP2);
Antimicrobial agent: 0.2 wt % benzalkonium chloride (Stepanquat® 50 NF);
Solvent: 3.2 wt % propanediol (Dupont Zemean™); and
Water: 94 wt %.

The acidity of the gels was measured by PH meter (Hanna Instruments). The acidity of the antimicrobial medical gels was determined to be between 6.5 and 8.5. This pH is suitable for use as a medical gel.

Additional Observations

The following observations were made regarding gels prepared as set out examples 1 and 6 above:

The gels were observed to exhibit pseudoplasticity (shear thinning) and to be readily dispensable from a squeeze bottle.

| Test No. | Solvent Type | Antimicrobial Agent (wt %) | Drop Diameter After Set period of time 0(h) | 0.5(h) | 1(h) | 8(h) | % Increase in drop diameter after 8 h |
|---|---|---|---|---|---|---|---|
| 1 | Propanediol (Zemea ™) | 0 | 10.6 | 32 | 33.5 | 38.5 | 263 |
| 2 | Propanediol (Zemea ™) | 3.2 | 10.6 | 30.3 | 32.3 | 37.0 | 249 |
| 3 | Propylene Glycol | 0 | 10.0 | 28.0 | 29.0 | 22.0 | 120 |
| 4 | Propylene Glycol | 3.2 | 12.3 | 28.0 | 29.0 | 24.6 | 100 |
| 5 | Glycerin 99% | 0 | 7.0 | 22.3 | 23.6 | 32.0 | 357 |
| 6 | Glycerin 99% | 3.2 | 4.0 | 22.6 | 24.0 | 29.3 | 632 |

The gels appeared to have a viscosity that is suitable for use as a medical gel

The gels appeared to be suitably lubricious for use as a medical gel.

The gels appeared to exhibit minimal air entrapment. This is believed to be due to the slow solubilization of the etherified hydroxyethylcellulose, which allows for time for air to evolve out of the gel.

REFERENCES

1. "Risk of *Staphylococcus Aureus* Transmission during Ultrasound Investigation," Journal of Ultrasound in Medicine, November 1989 8 (11): 619 20
2. "Burkhold eriacepacia Infections Associated with Intrinsically Contaminated Ultrasound Gel: The Role of Microbial Degradation of Parabens", Hutchinson J. et al., Infection Control and Hospital Epidemiology; 2004, vol. 25 No. 4
3. "An Outbreak of Pyodermas Among Neonates Caused by Ultrasound Gel Contaminated with Methicillin-Susceptible *Staphylococcus aureus*", Weist K. et al., Infection Control and Hospital Epidemiology; 2000, vol. 21 No. 12
4. "How the Tribune Analyzed Infection Cases," Chicago Tribune (Jul. 21, 2002)
5. "The Use of Economic Modeling to Determine the Hospital Costs Associated with Nosocomial Infections", R R Roberts et al., Clinical Infectious Diseases 36.11 (2003) 1424-1432
6. "A Systematic Audit of Economic Evidence Linking Nosocomial Infections and Infection Control Interventions, 1990-2000", American Journal of Infection Control 30.3 (2002): 145-52.
7. Brief to the National Advisory Committee on SARS and Public Health, Jul. 30, 2003. http://www.chica.org/nacsph.html
8. "Managing hospital infection control for cost-effectiveness: a strategy for reducing infectious complications", Haley R W, Chicago: American Hospital Publishing, 1986
9. "Notice to hospitals: important safety information on ultrasound and medical gels", Health Canada, Oct. 20, 2004, Available: www.hc-sc.gc.ca/hpfb-dgpsa/tpd-dpt/ultrasoundgel_e.html (accessed 2004 Oct. 27).
10. "Hospital Infections: Preventable and Unacceptable", Betsy Mccaughey, The Wall Street Journal, Aug. 14, 2008; Page A11
11. "An Epidemic, Toxin Gene-Variant Strain of *Clostridium difficile*", L. Clifford McDonald, M. D. et al.
12. "Risk of *Staphylococcus Aureus* Transmission during Ultrasound Investigation" Journal of Ultrasound in Medicine, November 1989 8 (11): 619 20
13. "Fomites and Infection transmission", Infection Control Today magazine, Nov. 7, 2006

The invention claimed is:

1. An ultrasound medical gel comprising:
   a) etherified hydroxyethylcellulose present in the medical gel at 1 wt % to 4 wt %;
   b) benzalkonium chloride present in the medical gel at 0.090 wt % to 0.110 wt %;
   c) 1,3-propanediol present in the medical gel at 3.0 wt % to 3.5 wt %; and
   d) water present in the medical gel at 80 wt % to 99 wt %.

2. The medical gel of claim 1, wherein the etherified hydroxyethylcellulose is present in the medical gel at between 2.2 wt % and 2.7 wt %.

3. The medical gel of claim 1, wherein at least some units of the etherified hydroxyethylcellulose are of the formula:

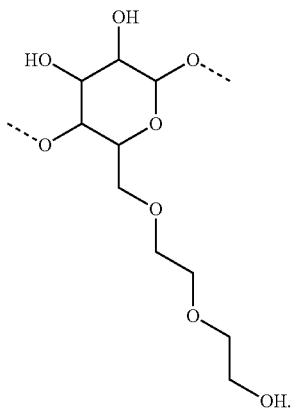

4. The medical gel of claim 1, wherein the etherified hydroxyethylcellulose is of the formula:

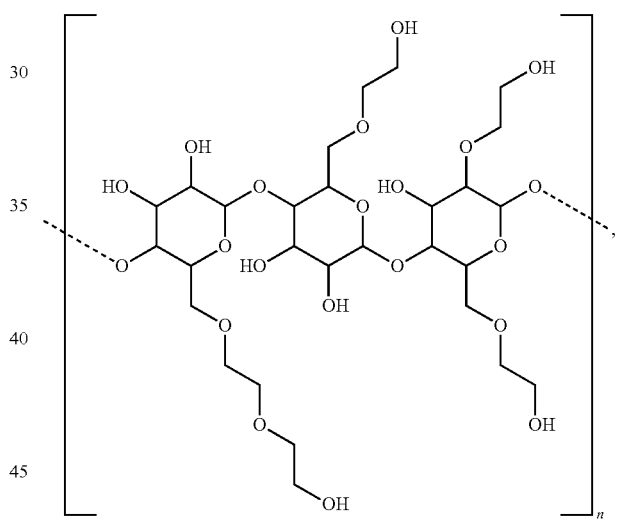

and n is a number greater than one.

5. The medical gel of claim 1, wherein the viscosity of the etherified hydroxyethylcellulose is about 100,000 cps when in a 2% aqueous solution.

6. The medical gel of claim 1 wherein the benzalkonium chloride is present in the medical gel at between 0.095 wt % and 0.105 wt %.

7. The medical gel of claim 1, wherein the 1,3-propanediol is present in the medical gel at between 3.1 wt % and 3.3 wt %.

8. The medical gel of claim 1, wherein the water is present in the medical gel at 93 wt % to 96 wt %.

* * * * *